US010959969B1

(12) United States Patent
Johnson (10) Patent No.: US 10,959,969 B1
(45) Date of Patent: *Mar. 30, 2021

(54) METHODS OF TREATING SARS COV-2 VIRUS WITH PROTOCATECHUIC ACID

(71) Applicant: Lanny L Johnson, Frankfort, MI (US)

(72) Inventor: Lanny L Johnson, Frankfort, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 16/947,759

(22) Filed: Aug. 14, 2020

Related U.S. Application Data

(63) Continuation-in-part of application No. 16/947,256, filed on Jul. 24, 2020.

(51) Int. Cl.
*A61K 31/192* (2006.01)
*A61P 31/14* (2006.01)
*A61K 9/16* (2006.01)
*A61K 9/00* (2006.01)

(52) U.S. Cl.
CPC .......... *A61K 31/192* (2013.01); *A61K 9/0014* (2013.01); *A61K 9/0019* (2013.01); *A61K 9/0043* (2013.01); *A61K 9/0053* (2013.01); *A61K 9/0073* (2013.01); *A61K 9/1617* (2013.01); *A61P 31/14* (2018.01)

(58) Field of Classification Search
CPC ........ A01N 37/40; A61P 31/14; A61K 31/192
See application file for complete search history.

(56) References Cited

PUBLICATIONS

C B Ou, et al., Erratum to "Protocatechuic acid, a new active substance against the challenge of avian infectious bursal disease virus" Poult. Sci. 91(7):1604-1609.
Ilana Agmon, et al., Spontaneous deformation of protocatechuic acid monohydrate crystals: crystallographic aspects, Proc. R. Soc. Lond. A 387, 3116330 (1983).
Ou C, Shi N, Yang Q, Zhang Y, Wu Z, et al. (2014) Protocatechuic Acid, a Novel Active Substance against Avian Influenza Virus H9N2 Infection. PLoS ONE 9(10): e111004.
Abida Kalsoom Khan, et al., Acta Poloniae Pharmaceutica—Drug Research, vol. 72 No. 4 pp. 643-650, 2015.
Amol B. Lende, et al., Anti-inflammatory and analgesic activity of protocatechuic acidin rats and mice, Inflammopharmacol (2011) 19:255-263.
C B Ou, et al., Protocatechuic acid, a new active substance against the challenge of avian infectious bursal disease virus, Poult Sci. Jul. 2012;91(7):1604-9, Abstract.
Charles Czank, et al., Human metabolism and elimination of the anthocyanin, cyanidin-3-glucoside: a 13C-tracer study, Am J Clin Nutr 2013;97:995-1003.
Chia-Yu Lin, et al., Anticoagulatory, Antiinflammatory, and Antioxidative Effects of Protocatechuic Acid in Diabetic Mice, J. Agric. Food Chem. 2009, 57, 6661-6667.

Chia-Yu Lin, et al., Antiglycative Effects of Protocatechuic Acid in the Kidneys of Diabetic Mice, IJ. Agric. Food Chem. 2011, 59, 5117-5124.
Dr. Sonam Bhatia, et al., Battle against Coronavirus: Repurposing old friends (Food bome polyphenols).
Kimtrele M. Williams, et al., Production of Protocatechuic Acid in Bacillus Thuringiensis ATCC33679, Int. J. Mol. Sci. 2012, 13, 3765-3772.
L.L. Theisen, C.P. Muller. EPs® 7630 (Umckaloabo®), an extract from Pelargonium sidoides roots, exerts anti-influenza virus activity in vitro and in vivo, Antiviral Research 94 (2012) 147-156.
Li-Yun Zheng, et al., Anti-hepatitis B virus activity of DDB-DU, a novel nucleoside analogue, in vitro and in vivo, European Journal of Pharmacology 702 (2013) 258-263.
Mitsuo Miyazawa, et al., Tyrosinase Inhibitor from Black Rice Bran, J. Agric. Food Chem. 2003, 51, 6953-695.
Omid Jalali et al., Reduced Bacterial Burden of the Skin Surrounding the Shoulder Joint Following Topical Protocatechuic Acid Application, JBJS Open Access d 2020:e19.00078.
Paola Vitaglione, et al., Protocatechuic Acid is the Major Human Metabolite of Cyanidin-Glucosides, J. Nutr. 137: 2043-2048, 2007.
Pattarapan Panthong, Anti-HIV-1 integrase activity and molecular docking of compounds from Albizia procera bark, Pharm Biol, 2015; 53(12): 1861-1866.
R. B. Cain, The Metabolism of protocatechuic acid by a vibrio, Biochem. J. (1961) 79, 298.
R. Masella et al., Protocatechuic Acid and Human Disease Prevention: Biological Activities and Molecular Mechanisms, Current Medicinal Chemistry, 2012, 19, 2901-2917.
R.W. Wood et al., Spontaneous deformation of protocatechuic acid crystals, Proceedings of the Royal Society of London, vol. 197, A. (Jun. 22, 1949).
Sahil Kakkar, et al., A Review on Protocatechuic Acid and Its Pharmacological Potential, ISRN Pharmacology, vol. 2014, Article ID 952943, 9 pages.
Shannon Reagan-Shaw et al., Dose translation from animal to human studiesrevisited, FASEB J. 22, 659-661 (2007).
Sherif T. S. Hassan, et al., Hibiscus sabdariffa L. And Its Bioactive Constituents Exhibit Antiviral Activity against HSV-2 and Anti-Enzymatic Properties against Urease by an ESI-MS Based Assay, Molecules 2017, 22, 722.
Siva Ganesh M, et al., A Novel Approach for Rationale Selection of Medicinal Plants Against Virusesvia Molecular Docking Studies.
Taofeek O. Ajiboye, et al., Involvement of oxidative stress in protocatechuic acid-mediated bacterial lethality, MicrobiologyOpen. 2017;6:e472.
Wei Chen, et al., Pharmacokinetics of protocatechuic acid in mouse and its quantification in human plasma using LC-tandem mass spectrometry, W. Chen et al. / J. Chromatogr. B 908 (2012) 39-44.
Wikipedia, Protochatechuic acid, last edited on Jun. 6, 2020.

(Continued)

*Primary Examiner* — Yong S. Chong
(74) *Attorney, Agent, or Firm* — Stonebridge IP, PLLC (57) ABSTRACT

The present disclosure provides methods for killing the SARS CoV-2 virus in mammals and treating the Coronavirus Disease-19 (Covid-19) in mammals including humans using compositions including protocatechuic acid. The present disclosure provides methods and pharmaceutical and nutraceutical compositions that reduce or substantially eliminate the SARS CoV-2 virus in mammals. In one embodiment, a method of treating a mammal with Covid-19 is provided comprising administering protocatechuic acid to a mammal in need of such treatment a therapeutically effective amount of a protocatechuic acid composition.

20 Claims, 3 Drawing Sheets

(56) References Cited

PUBLICATIONS

Xuan Luo, et al., Study on the Anticoagulant or Procoagulant Activities of Type II Phenolic Acid Derivatives, Molecules 2017, 22, 2047.

Yongxia Guo, et al., Protocatechuic acid (PCA) induced a better antiviral effect by immuneenhancement in SPF chickens, Microbial Pathogenesis 114 (2018) 233-238.

Yoshimasa Nakamur et al., Toxic Dose of a Simple Phenolic Antioxidant, Protocatechuic Acid, Attenuates the Glutathione Level in ICR Mouse Liver and Kidney, J. Agric. Food Chem. 2001, 49, 5674-5678.

Yoswaris Semaming, Pharmacological Properties of Protocatechuic Acid and Its Potential Roles as Complementary Medicine, Evidence-Based Complementary and Alternative Medicine vol. 2015, Article ID 593902, 11 pages.

Zakay-Rones et al., Inhibition of Several Strains of Influenza Virus in Vitro and Reduction of Symptoms by an Elderberry Extract, Journal of Alternative and Complementary Medicine, vol. 1, No. 4, 1995, 361-369.

Zeraik ML, Petronio MS, Coelho D, Regasini LO, Silva DHS, et al. (2014) Improvement of Pro-Oxidant Capacity of Protocatechuic Acid by Esterification. PLoS ONE 9(10): e110277.

METHODS OF TREATING SARS COV-2 VIRUS WITH PROTOCATECHUIC ACID

CROSS REFERENCE TO RELATED APPLICATIONS

This application is a continuation in part of U.S. application Ser. No. 16/947,256 filed Jul. 24, 2020, which is herein incorporated by reference in its entirety.

BACKGROUND OF THE DISCLOSURE

Field of the Invention

This disclosure is generally directed to methods of treatment of the SARS Cov-2 virus in mammals including administration of a composition comprising protocatechuic acid (PCA) in a pharmaceutically effective amount to a mammal, including humans, that is in need thereof.

Description of the Related Art

The COVID19 pandemic continues with no end in sight. At present, there is no definitive treatment or vaccine for SARS CoV-2 virus. There are mitigation measures including 'stay at home', social distancing measures, and use of face masks. The public compliance of such is lacking because of the perception there is no actual benefit since the measures are not killing the virus. What is needed at present are ways to kill the SARS CoV-2 virus. Recent studies have demonstrated that a nutraceutical protocatechuic acid (PCA) was virucidal against live SARS CoV2 virus upon contact with PCA in an aqueous medium.

The World Health Organization named the new coronavirus SARS-CoV-2, and the disease, COVID-19 (Corona-Virus Disease-19). Corona viruses are common and have been known for many years. People around the world commonly get infected with human coronaviruses: 229E, NL63, OC43, and HKU1. However, it has become apparent that the SARS-CoV-2 is unlike any other coronavirus; i.e.; MERS, SARS-CoV, and the common cold. SARS-COV-2 is unique clinically in that it is highly contagious. It rapidly became a pandemic and it is very aggressive. It affects not only the respiratory system but there are pathological manifestations in the skin, brain, liver and kidney as well.

SARS-CoV-2 differs in molecular structure from other coronavirus. It is known that prion—like domains exist with a distribution in the coronavirus that are unlike prion-like domains in other viruses and which may play important functional roles in transmission. The introduction of the prion to the molecular structure of the SARS-CoV-2 may require different and unique therapeutic reagents or methods. Prion is a term first used to describe the mysterious infectious agent responsible for several neurodegenerative diseases found in mammals, including Creutzfeldt-Jakob disease (CJD) in humans. The word itself derives from 'proteinaceous infectious particle' and it refers to the initially heretical hypothesis that the infectious agent causing those diseases consists only of protein with no nucleic acid genome. All previously known pathogens contain nucleic acids, which enable them to reproduce. The prion hypothesis explained why the mysterious infectious agent is resistant to ultraviolet radiation, which breaks down nucleic acids, but is susceptible to substances that disrupt proteins.

The clinical manifestations of SARS Co-2 are unique and differ from other respiratory virus. SARS Co-2 is very contagious. At the same time, the clinical manifestation may vary from no symptoms, mild symptoms, and for some, very severe symptoms and/or death. Although the primary pathology is in the respiratory system (a lung infection), this virus has new and expanded clinical manifestations beyond prior coronal viral observations including pulmonary modes. In addition, there have been heart, skin, and brain manifestations. Its clinical manifestations also include a severe inflammatory component called a 'cytokine storm' in the lungs. There is also thrombosis in other areas of the body beyond the lungs that has resulted in amputation of the limbs. The numbers of those infected and those dying is large.

COVID-19 is thus a pathological and clinical enigma. There is no known prophylactic drug. There is no specific therapeutic drug. There is no drug or treatment with the present prospect of translation to clinical practice. The present scientific therapeutic measures are limited to testing and tracking after which recommendations can be made for social distancing and face masks. Quarantines have been used. State and local governments have mandated non-essential business shutdowns and limited public gatherings. These are after the fact measures and none are therapeutic. Testing or tracking of an entire population is not realistic and, in any case, false positives and negatives exist with all testing. Add to that, a pre-symptomatic patient is a likely cause of transmission before they have recognizable symptoms. In addition, it is recognized that there are certain subjects, perhaps 20% of those with the disease that are super spreaders yet are only identified after the fact. The fact remains that COVID-19 is not well understood and is highly contagious.

The pandemic is rapidly evolving and there is every expectation it will continue since the epidemiology of this new strain is yet to be established. Even though its identification was established, the virus has spread globally, causing thousands of deaths and having an enormous impact on international health systems and economies. The only present means of containing this very contagious virus is by mitigation. There is no known established treatment.

Crystals may provide a therapeutic application by their physical nature. They have known cytotoxic properties which can achieve a therapeutic result. It is known that the physical properties of crystals can have an antimicrobial property independent or in conjunction with their biochemical properties. Their many sharp edges have the potential to physically disrupt a microbe's integrity.

The coronaviruses are particularly physically vulnerable. The covering of the coronavirus is surrounded by many projections like a crown. The projections are called prongs or spikes. These spikes are the virulent contact agent with the host cell. They penetrate the human cell and the infection is then propagated. The spikes and underlying thin wall coating of the viral body are vulnerable to physical disruption. Physical disruption is thus one potential method of stopping the cellular invasion and the clinical disease. Crystals have a physical structure that is irregular, rough, and sharp with potential to physically disrupt a microbes' spikes and covering.

Accordingly, there is a need and an opportunity for prevention and treatment to expand beyond or in conjunction with the chemical methods to one that is physical disruption and one that is effective despite various prion mutations. The use of crystals presents the possibility of creating an antiviral agent capable of protecting from or destroying SARS-CoV-2.

Protocatechuic acid crystals like other crystals are typically observed and considered only in the dry state. However, it known that PCA retains various crystalline shapes while in a liquid medium. The PCA crystal was first reported in liquid to be in three different forms in 1949. The following publication from 1949 is extensively illustrated. See https://royalsocietypublishing.org/doi/10.1098/rspa.1949.0064 Robert Williams Wood. Published:22 Jun. 1949. htttps://doi.org/10.1098/rspa.1949.0064.

In 1983, Agmon et al. supported Wood's work and showed that some crystalline shapes were stable in form and other were rapidly changing in liquid. See Agmon I, Herbstein F H, Thomas J M. Spontaneous deformation of protocatechuic acid monohydrate crystals: crystallographic aspects. Proc. R. Soc. Lond. 1983. A387311-330. http://doi.org/10.1098/rspa.1983.0062.

SUMMARY OF THE INVENTION

In embodiments, the present disclosure provides methods for killing the SARS CoV-2 virus in mammals and treating the Coronavirus Disease-19 (Covid-19) in mammals including humans using compositions including protocatechuic acid (PCA). The present disclosure provides methods and pharmaceutical and nutraceutical compositions that reduce or substantially eliminate the SARS CoV-2 virus in mammals and treat Covid-19.

In one embodiment, a method of treating a mammal with Covid-19 is provided comprising administering PCA to a mammal in need of such treatment a therapeutically effective amount of a protocatechuic acid (PCA) composition.

The disclosure also provides methods and compositions that effectively deliver PCA compositions to an affected mammal including humans. This includes intravenous administration and oral administration. The present invention also provides compositions and methods for use in the treatment of Covid-19 to localized affected areas of a mammal as well. This would include the skin, lungs, and nasal cavities. The present disclosure also provides compositions and methods for use in the treatment of a variety of symptoms related to Covid-19.

In oral ingestion embodiments, the ready absorption places the PCA in solution in the plasma. As a result, it is known to profuse the entire body; cells, tissues and organs which will kill SARS Co 2 on contact. This will last throughout the known presence of PCA in the mammalian body for several days. Additional interval doses over time may give a continued effect. The PCA known metabolism is that it is subsequently found in urine and feces intact and as subsequent metabolites.

In the preferred embodiments of intraperitoneal route of application, the ready absorption places the PCA in solution in the plasma which will kill SARS Co 2 on contact. This will last throughout the known presence of PCA in the mammalian body for several days. The PCA known metabolism is that it is subsequently found in urine and feces intact and as subsequent metabolites. Additional interval doses over time may give a continued effect.

In embodiments of intravenous route of application, the administration places the PCA in solution in the plasma which will kill SARS Co 2 on contact. This will last throughout the known presence of PCA in the mammalian body for several days. The PCA known metabolism is that it is subsequently found in urine and feces intact and as subsequent metabolites. Additional interval doses over time may give a continued effect.

Also disclosed is a method of treating a pathological condition caused by SARS CoV2 virus, comprising the coating of skin, oral cavity, nares, nasopharynx, and pulmonary tree with PCA in either amorphous or crystalline form.

Also disclosed are methods of treatment of the pathological condition caused by the SARS CoV2 virus comprising the intravenous and intraperitoneal route.

In embodiments, the present disclosure provides multiple routes of therapeutic delivery of PCA. Normal size crystals (e.g., approximately 177 μm) and powder may be delivered by the oral route. Smaller sized crystals and particles may also be used for intravenous, intraperitoneal and aerosol delivery to a patient.

The therapeutic compositions and compounds may be administered, for example, orally and topically. The therapeutic compositions and compounds may also be administered by various conventional routes including, for example, oral, topical, buccal, injection, pulmonary, intravenous, inhalant, subcutaneous, sublingual, and/or transdermal.

Further by way of example, the pharmaceutical composition can comprise: PCA and a pharmaceutically acceptable carrier. By way of example, the pharmaceutically acceptable carrier can be selected from, but not limited to, any carrier, diluent or excipient compatible with the other ingredients of the composition.

Further by way of example, the pharmaceutical composition can comprise PCA and an acceptable delivery carrier. By way of example, the delivery can be formulated and administered as known in the art, e.g., for topical, oral, buccal, including lozenges, injection, intravenous, inhalant, subcutaneous, sublingual and/or transdermal. Further, said topical delivery carrier may be formulated and administered to any surface or cavity of the body.

By way of example, the acceptable delivery can be selected from any dermal or transdermal carrier compatible with the other ingredients of the composition. In some embodiments, the acceptable delivery carrier is a biodegradable microsphere or a slow release bioabsorbable material. By way of example, the acceptable delivery carrier can be selected from 50/50 D, L lactide/glycolide or 85/15 D, L lactide/glycolide, both of which are amorphous physically and, therefore, are non-reactive when used as a carrier in a composition that is delivered in or to the body.

In embodiments, the pharmaceutical composition comprising PCA may be formulated for an aerosol spray. The aerosol spray may include PCA, a liquid vehicle, and a stabilizer. The liquid vehicle may include water or an alcohol and the stabilizer may include an oil. In preferred embodiments, the oil is an essential oil. In preferred embodiments, the essential oil may be lemon oil. In embodiments, the aerosol spray compositions may comprise principally protocatechuic acid, liquid vehicle, and stabilizer as the main ingredients. In preferred embodiments, the aerosol spray compositions may comprise only protocatechuic acid, a liquid vehicle, and a stabilizer.

Other features and aspects will be apparent from the following detailed description, the drawings, and the claims.

BRIEF DESCRIPTION OF THE DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, products, and/or systems, described herein. However, various changes, modifications, and equivalents of the methods, products, and/or systems described herein will be apparent to an ordinary skilled artisan.

Protocatechuic acid (PCA) (IUPAC: 3,4 dihydroxybenzoic acid) is found throughout nature; in the soil and plants. PCA is the primary metabolite form cyanidin-3-glucoside, a dye that makes blueberries blue and cherries red. PCA is common in the human diet in most vegetables and fruits. The human bowel bacteria manufacture small amounts daily. PCA upon ingestion perfuses all the cells and tissues of the human body in matter of a few minutes. The entire metabolism is known with duration of eight hours prior to excretion in the urine and feces.

PCA is safe for human consumption. PCA has an existing FDA G.R.A.S. designation as Generally Recognized As Safe as a flavoring substance. Its FEMA number is 4430. PCA is non-toxic. There are no known allergy or mutagenic effects. PCA is a powerful antioxidant; 10 times more powerful than vitamin E.

Antioxidants are fundamental to health. PCA is a powerful anti-inflammatory reagent. Inflammation is known to be the common denominator of all disease. PCA enhanced the genetic expression in vitro studies of local growth factors in human and rabbit synovium, rodent skin and human osteoblasts and mesenchymal stem cells to produce bone. There are known to be many, and varied, health benefits of protocatechuic acid.

Infection is a serious comorbidity in some COVID19 patients calling for supplemental antibiotic. Therefore, the additional antibiotic properties of PCA could be important in treating such patients.

PCA is nontoxic. Toxicity is greater than 5000 mg/kg body weight in female rats. The conversion to a human relative dose to exceed safety would be 350,000 milligrams per day for a 70-kilogram human. This amount is not likely to be ingested at once or over a period of time.

A recommended oral dose for humans could be a minimum of 500-1000 milligrams per day.

The present production methods for PCA are biochemical. The products are absent of trace metals. PCA is readily available in large amounts from several international manufacturers.

PCA may be a physical crystal retaining this condition in air (dry) as well as in a liquid vehicle or environment. The physical shape is one of sharp edges and projections, even shown to be needle-like in solution. The irregular sharp projections may physically disrupt a bacterial biofilm and the prongs and coating of SARS CoV2 upon contact. Compositions comprising PCA have been shown effective for antimicrobials and methods for wound healing. PCA is a biofilm destroyer for MRSA and *Pseudomonas*. Evidence of such resulted in U.S. Pat. No. 10,004,705. This patent was based upon studies performed by ASTM E-2647 Drip Flow Biofilm Reactor. The methodology is to spray metal and or fabric with an alcohol solution of PCA. Upon drying there is a residual coating of PCA. The PCA forms a protective coating. The biofilms were flowed over the articles for 48 hours rendering the following findings: 99.999% kill of these biofilms. The safety and effectiveness for controlling potential pathogens on human skin has also been demonstrated. There is no skin irritation.

PCA's Mode of Action on SARS CoV2 may include multiple modes of action. Crystalline sharp shapes for disruption, low pH, anti-protease, docking blocking, enhancing the cellular and hormonal immunity, anti-tyrosinase, anti-thrombosis. Traditional antimicrobials function chemically or biochemically. Their biochemical inter-action disrupts the viral interaction with the host and/or physically disrupts the virus prongs or wall. Crystals by their physical nature have similar known cytotoxic properties.

Crystals may include atoms, ions or biomolecules, and may cause tissue injury, inflammation and re-modelling. This may be due to nucleation or crystal growth from a seed crystal formed on a surface medium, for example tubular epithelial cells, urolithiasis forming at Randall's plaques, calcifications in injured tendons, damaged cartilage or atheromatous vascular lesions, crystal formation itself causes tissue injury and inflammation, for example in gouty arthritis, pulmonary silicosis or asbestosis, cholesterol crystals driving atherogenesis and in oxalate, cystine or urate nephropathy. Crystals may also trigger tissue inflammation via the NLRP3 inflammasome and caspase-1-mediated secretion of IL-113 and IL-18. Crystals may also exert direct cytotoxic effects leading to necrotic rather than apoptotic cell death.

This shows that the physical properties of crystals have an antiviral property, independent or in conjunction with their biochemical properties. They can physically disrupt virus integrity.

The coronaviruses are particularly vulnerable. The covering of the coronavirus is surrounded by many projections like a crown. The projections may be called prongs or spikes. These spikes are the virulent contact agent with the host cell. They penetrate the human cell and the infection is propagated.

The spikes and underlying thin coating are vulnerable to physical disruption. Physical disruption is one potential method of stopping the invasion and the clinical disease. Crystals have a physical structure that is irregular, rough, and sharp with potential to physically disrupt virus spikes and cover.

In a related context, PCA is also known as a broad-spectrum antibacterial biofilm destroying antibiotic when coating of cloth and or metal surfaces (U.S. Pat. No. 10,004,705). PCA has the physical properties of a crystal with sharp protrusions that can disrupt the coating of viruses. See Ajiboye T O, Habibu R S, Saidu K, et al. Involvement of oxidative stress in protocatechuic acid-mediated bacterial lethality. Microbiologyopen. 2017; 6(4):e00472. doi: 10.1002/mbo3.472.

The crystal structure of a reagent causes physical disruption of a viral coating resulting in viral death. The PCA crystal was first reported to be in three forms in 1949 as mentioned above. The present-day significance is that PCA in a fluid environment retains its crystalline anti-viral properties. The crystalline physical nature may be constantly changing in solution.

The clinical importance is the fact that PCA in a liquid (water, alcohol, or other vehicles) retains various crystalline form of varying shapes, but all with sharp edges. This crystalline antiviral factor exists whether in a liquid vehicle or dried on a surface.

Figure 1:
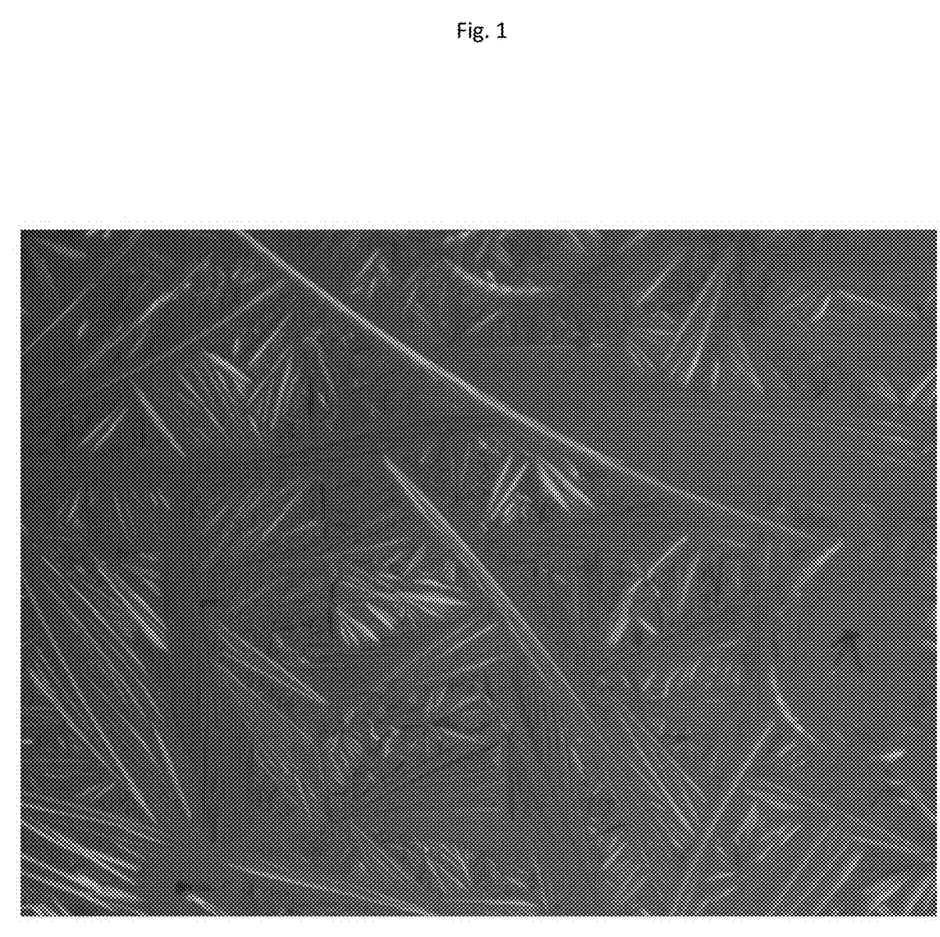
FIG. 1 shows crystals of PCA upon drying on a surface.

FIG. 1 shows crystals of PCA upon drying on a surface.

Figure 2:
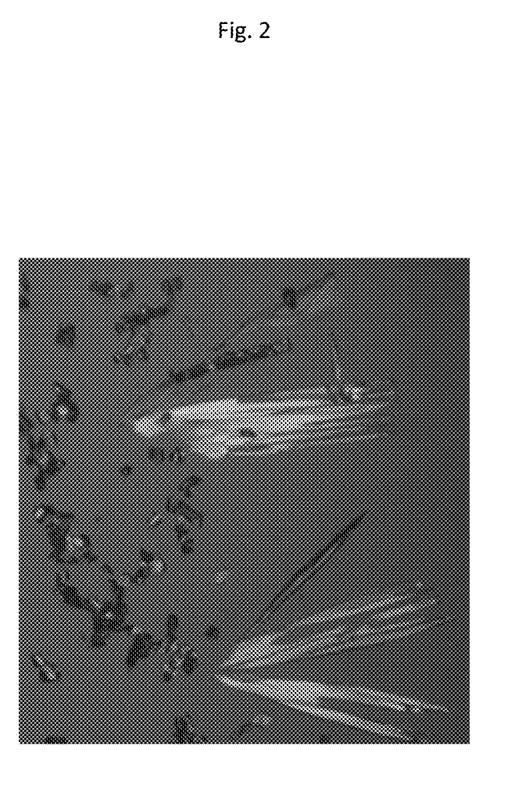
FIG. 2 shows a photomicrograph of crystals of PCA in a water droplet.

FIG. 2 shows a photomicrograph of Crystals of PCA in a water droplet under high power magnification. This figure also shows small prism crystals not yet converted to needles as this was just 30 minutes after visually dissolved in distilled water.

Figure 3:
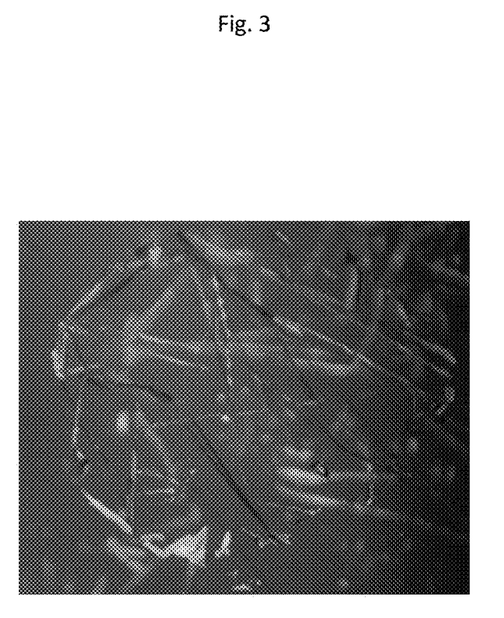
FIG. 3 shows a photomicrograph of crystals of PCA dissolved in ethanol.

FIG. 3 shows a photomicrograph of crystals of PCA dissolved in ethanol in 30 minutes. The high-power magnification shows multiple needle shaped crystals.

Therefore, the virucidal property would exist for dry PCA on a surface. The SARS CoV2 virus in the liquid droplet would engage the dry PCA and crystal formation could occur immediately upon changing the environment to liquid. The PCA crystal is only slowly 1.24% soluble in water and its transition to the fluid state would be slow and the virus may be inactivated before the PCA in any significant amount was soluble. The SARS CoV2 virus would be inactivated upon engagement with PCA crystal.

The associated in vitro studies provided below replicated the clinical environment in reducing transmission. The PCA coating on a hard or cloth article was virucidal for SARS CoV2 virus. The same would be for any coating on skin or other like surfaces.

Accordingly, in preferred embodiments, the PCA has at least some liquid or moisture present. Preferably, the PCA may be dissolved in water, alcohol, saline, including saline 0.9% salt, or some other liquid, including droplets. Once dissolved in a liquid, the PCA may become crystalline in form and may then physically disrupt a virus and become virucidal. Nevertheless, dry PCA powder in amorphous or crystalline form is also included in this disclosure.

Drugs that change the pH at the surface of a cell membrane inhibit the fusion of the virus to the cell membrane. It can also inhibit nucleic acid replication, glycosylation of viral proteins, virus assembly, new virus particle transport, virus release, and other processes to achieve its antiviral effects. PCA has an acid pH of 5.4 which is disruptive to viral coating.

COVID-19 main protease (Mpro) is the key enzyme of coronavirus which plays a crucial role in virus replication and transcription, which can be targeted to retard the growth of virus inside the host. One of the major proteins of COVID 19 is Mpro (main protease), also referred to as the '3C-like protease' belonging to the proteases class of hydrolytic enzymes. This enzyme plays a key role in the processing of pp1a (responsible for generating copies of viral genome) and pp1ab (responsible for generating viral genome) as involved in their proteolytic cleavage at the conserved residues among COVID 19 genome.

These can assemble to give rise to virions inside the host cell and thus, replicate to produce multiple copies. Mpro can act as potential target for structure-based drug discovery as this enzyme not only involved in autocatalytic cleavage of itself and key viral enzymes, as well as lacks any close homologues among human hosts. Targeting this enzyme using suitable protease small molecule inhibitor holds immense potential to curb virus replication and transcription which are critical steps in virus life cycle. PCA has anti-protease properties.

Molecular docking is an important tool in computer-based drug design and drug discovery which helps to predict the small ligand conformation and orientation (Docking pose) within the active sites of the target receptor protein.

Protocatechuic acid has high docking score (−9.8) and importantly protocatechuic acid derivatives show comparatively better pharmacokinetic predictions and lead likeness, along with the ease of synthesis. PCA is bioavailable by oral intake.

PCA as one of the polyphenolic scaffolds have affinity to bind with substrate-binding pocket of COVID-19 virus Mpro, which is highly conserved among all CoV Mpros. This supports the fact that small molecule inhibitors (PCA) targeting Mpro or in combination with other adjuvant therapies could provide an effective therapeutic regime to fight against all coronavirus associated diseases.

The top six docked polyphenols are mainly derivatives of protocatechuic acid polyphenols. Their pharmacokinetics point out the poor bioavailability of these polyphenols if taken individually as active compounds. However, protocatechuic acid (1 Lipinski violation) derivative among all have shown better pharmacokinetic profiles.

PCA provides enhanced hormonal and cellular immunity. This is critical as COVID19 effects the immunity in most severe clinical cases.

PCA has anti-inflammatory properties as a catabolic cytokine blocker. One of the ways the human body responds to SARS CoV-2 is with a massive anti-inflammatory inflow of fluids to already compromised lungs.

PCA has powerful anti-inflammatory properties with clinical relevance for the cytokine storm associated with clinical SARS CoV2 infections. It also reduces the C-reactive protein. PCA acts as a tyrosinase inhibitor in other applications.

PCA, may slightly increase the prothrombin time. This is especially beneficial for prophylactic or therapeutic treatment in COVID19 clinical cases that may have thrombosis.

An oral dose for humans could be a minimum of 500-1000 milligrams per day. The dose for administration may be interdependent on the other factors. The dose for aerosol spray, ventilation and/or nebulizer, may be a solution. It could be as low as, for example, 25 µM in water. It could be 1 to 30% by weight depending upon a vehicle's solubility properties.

As one example, if it is 1% by weight, then if sprayed 3 times, the resultant dose concentration becomes 3%. If a certain concentration is delivered intravenously the variables include speed of flow and duration.

The inherent impedance of travel varies with the individual so that the amounts delivered to the target, e.g., the lung would depend upon the delivery factors in a ventilator and the fluid, bronchial and alveolar blocked with mucous for example.

One example dosage could be 50 mg/kg, IV, every 6 hours for 4 days.

In aerosol or liquid spray compositions, water may be the vehicle for treatment of mucous membranes of the nose, mouth, pharynx, respiratory tree, and lungs. The compositions may be sprayed, misted, or fogged onto mammalian and human skin, the lungs and/or nasal cavities, etc., to kill and protect from the Covid 19 SARS-Co-2 virus. Electrostatic means of spraying including sanitizing or disinfection are also included.

The term fog can generally mean a cloudlike mass or layer of minute droplets including crystals. The term fogging can mean to cover or envelop with a fog. Fogging can be accomplished with fogging or disinfecting machines well known in the art. For example, medical grade disinfecting fogging machines can preferably be used. Portable medical grade fogging machines are also preferred. Large scale industrial fogging machines can be used for large facilities like hospitals, stadiums, public entertainment facilities, etc.

A fog machine, fog generator, or smoke machine is generally a device that emits a dense vapor that appears similar to fog or smoke. An artificial fog may be used in large scale applications, and smaller, more affordable fog machines can be used for more localized applications. Fog machines typically used in a variety of industrial, training, health care, and military applications are contemplated. Typically, fog is created by vaporizing proprietary water and glycol-based or glycerin-based fluids (or through the atomization of mineral oil). This fluid (often referred to colloquially as fog juice) vaporizes or atomizes inside the fog machine. Upon exiting the fog machine and mixing with cooler outside air the vapor condenses, resulting in a thick visible fog.

Spraying is generally a fluid flying in small drops or particles for example mechanically created and blown and may be a jet of vapor or finely divided liquid and can be produced by a device (such as an atomizer or sprayer) by which the spray is created, dispersed, and/or applied.

A spray may be considered a dynamic collection of drops dispersed in a gas. The process of forming a spray is sometimes referred to as atomization. A spray nozzle may be used to generate a spray. Sprays may be used to distribute liquid drops over some cross-sectional area and/or to generate a liquid surface area.

An aerosol spray may be a type of dispensing system which creates an aerosol mist of liquid particles. It can be used with a can, plastic or glass bottle, or other container, that contains a payload and propellant under pressure. When the container's valve is opened, a payload is forced out of a small hole and emerges as an aerosol or mist. As propellant expands to drive out the payload, only some propellant may evaporate to maintain a constant pressure. The droplets of propellant may evaporate rapidly, leaving the payload suspended as fine particles or droplets.

In preferred embodiments, the liquid vehicle includes water or a low boiling point alcohol and/or alcohol combination ranging from about 0° C. to about 100° C. The alcohol may include methanol and/or butanol, but preferably ethanol and/or propanol for human use.

Low boiling point alcohols can include alcohols such as methanol, ethanol, 1-propanol, 2-propanol, 1-butanol, 2-butanol, 2-methyl-1-propanol, 2-methyl-2-propanol, 1-pentanol, 3-methyl-1-butanol, 2,2-dimethyl-1-propanol, and cyclopentanol.

An essential oil is generally a concentrated hydrophobic liquid containing volatile (easily evaporated at normal temperatures) chemical compounds extracted from a plant. Essential oils are also known as volatile oils, ethereal oils, aetherolea, or as the oil of the plant from which they were extracted. In preferred embodiments, the essential oil may comprise orange, mint, peppermint, cedarwood, lemon, southern blue gum, evergreen, clove, and/or spearmint.

Additional possible ingredients include glycerin, propylene glycol, sodium benzoate, as well as sanitizers and disinfectants. Propylene glycol may be a vehicle for topical application and/or for aerophilization.

Example 1

Saliva testing was performed with PCA. This example replicated the practical clinical use of a lozenge to deliver the therapeutic crystals of PCA to the oral cavity and tongue's part of the pharynx and substantiated the lasting duration of PCA coating on those anatomical structure's irregular surfaces of the oral pharynx.

It was initially observed in photomicrographs of PCA powder on glass with polarized light that there were no observable crystals. A human subject then took raw PCA powder into the mouth and allowed for salivation. After approximately 5 minutes a photomicrograph of the saliva/PCA on glass with polarized light showed small black powder and small fluorescent crystals. The fluorescent crystals could be more clearly seen under higher power magnification.

After another approximately 10 minutes, the photomicrographs of the saliva/PCA on glass with polarized light showed more needle shaped crystals. After another approximately 5 minutes, even more needle shaped crystals were visible. There was evidence that the crystals migrated in the fluid by gravity. At this point, a polarized light photomicrograph showed transition shapes although primarily rhomboid, perhaps due to enzymes in the saliva.

Further photomicrographs showed smaller crystals in wet saliva not yet subject to drying. On high power in the wet saliva, powder changing to crystals could be seen with polarized light. That is, there were fewer powder clumps as the powder continued to dissolve and change to crystals. Scraping of the lower lip of the human subject showed the powder had transitioned to crystals that could be seen in polarized light and showed a mixture of rhomboid and needle shapes.

One hour after oral lavage, the human subject tongue was scraped placed on a histology slide and subjected to polarized light showing a multitude of rhomboid and some needle shaped crystals. High-powered photomicrographs showed a single black powder clump surrounded by polarized crystals. This is representative of a transition from a powder to a crystal in a liquid environment.

Example 2

This example shows nasal hair Coating with Protocatechuic acid crystals. The nasal hair has a natural filtering function. Therefore, a PCA coating can be applied with raw crystals, but also with a variety of vehicles; water, glycerin, propylene glycol and or mixtures with alcohols that put the powder into small crystals intimately attached to the hair. Photomicrographs of alcohol solution of PCA on hair with polarized light show the intimacy of crystals on the hair. Photomicrographs show crystals covering the end of the cut hair.

In another experiment, protocatechuic acid crystals from a propylene glycol vehicle were applied to nasal hair. The protocatechuic acid crystals had a different physical appearance at time zero than in the alcohol vehicle of Example 1. This was seen in high power polarized light at junction of fluid and air. There was a vertical line of demarcation. The visualization of the crystals on the hair was delayed for 5 minutes. A propylene glycol coating on the hair and the crystals was evident in the fluid. The shape of the crystals was different from that seen from alcohol vehicle. After a few more minutes crystals were seen on the hair with intimate position. The use of PCA in solution will result in the coating of hair. The use as an adjunct to the mitigation of the SARS CoV 2 virus by coating the hairs of then nares has been demonstrated.

Example 3

Example 3 demonstrates the results studies utilizing a methodology replicating the clinical therapeutic environment whereby the PCA crystal engages the SARS CoV-2 virus in an aqueous environment. These studies demonstrate the effectiveness of Protocatechuic Acid (PCA) against SARS-CoV-2, the causative virus for COVID19.

The Test Article (TA) used for this study was Protocatechuic Acid (PCA). The TA was received as an off-white powder. The PCA solution was prepared to be 30% PCA w/v in Ethanol. The PCA was prepared in 5 g increments to pre-warmed 50-60 mL ethanol until dissolved for a total of 30 g PCA in the solution. Additional ethanol was then added volumetrically to be equivalent to 100 mL.

The Test Substrates (TS) were a Plastic-type material sourced from a clear plastic laboratory bottle (Corning 431731 Octagonal bottle, 150 mL), cloth (the top layer of a N95 mask [3M 8210]), and a Sponsor-provided wire mesh to serve as a substrate for the TA. All test substrates were cut to approximately 1"×1" in size. The test substrates were submerged into the PCA solution and dried horizontally to allow for even coating. After the substrate was thoroughly dried, the test substrate was re-submerged into the PCA solution for an additional coating.

The Test Virus used for this study was 2019 Novel Coronavirus, Isolate USA-WA1/2020 (SARS-CoV-2). The virus was stored at approximately −65° C. prior to use. The multiplicity of infection (MOI) was 0.01 $TCID_{50}$/cell.

The Cell Culture used for the $TCID_{50}$ test was African Green Monkey Kidney Cells (Vero E6 cells) that were maintained in Dulbecco's Minimum Essential Medium with 10% fetal calf serum (DMEM-2). All growth media contained heat-inactivated fetal calf serum and antibiotics.

The test design is shown below in Table 1. This test assesses the TA on a substrate in various conditions as shown in Table 1.

The Test Substrate was coated with PCA as described above. The test substrates were treated with PCA twice and allowed to fully dry overnight. In general, the time from the first coat to the next day's virus exposure was approximately 24 hours.

The treated Test Substrate plus TA was placed into a sterile 6 well cell culture plate and approximately 100 µL total of a ≥1×10⁶ $TCID_{50}$/mL SARS-CoV-2 virus was such that 50 µL of virus was layered on each sides of the treated test substrates. This was the procedure used for the initial Day 1 experiment.

For the confirmatory test, in an attempt to increase the recorded titer of the controls, the treated Test Substrate plus TA was placed into a sterile 6 well cell culture plate and the same amount of virus was layered onto both sides of the test substrate. However, an addition 50 µL of DMEM was added to each side to reduce the inactivation of the virus due to desiccation. Additionally, a glass coverslip was also added to help mitigate against evaporation.

After application of the virus, the virus was contact with the Test substrates for approximately 10 minutes (Groups 1, 2, and 3, Control groups 7, 8, and 9), 60 minutes (Groups 4, 5, and 6, Control Groups 10, 11, and 12). Each substrate per time per test article was performed in duplicate.

A cell culture-only control was included to indicate that cells without any TA or virus remain healthy throughout the assay. Virus-only controls without substrate was added for each timepoint to verify that the assay was performing as expected.

After the incubation time, the treated substrate was washed with 1 mL of cell culture media (DMEM-2) for approximately 5-10 minutes within the 6 well cell culture plate and the glass cover slip removed if necessary. This was the equivalent to a 10-fold dilution. The plate was gently stirred via an orbital shaker to enhance the recovery of the virus.

For the $TCID_{50}$, the cell culture media (DMEM-2) used to wash the Test Substrate was serially diluted 10 fold and transferred into respective wells of a 96-well plate which contained a monolayer of African Green Monkey Kidney Cells (Vero E6 cells) for titration. The $TCID_{50}$ assay was performed non-GLP according to IITRI Standard Operating Procedures for the assay. The $TCID_{50}$ titers was calculated using the method of Reed-Muench.

TABLE 1

| | Study Design | |
|---|---|---|
| Group | Test and Control Groups | PCA |
| 1 | Plastic (10 minute exposure) | 2 replicates |
| 2 | Cloth (10 minute exposure) | 2 replicates |
| 3 | Mesh (10 minute exposure) | 2 replicates |
| 4 | Plastic (60 minute exposure) | 2 replicates |
| 5 | Cloth (60 minute exposure) | 2 replicates |
| 6 | Mesh (60 minute exposure) | 2 replicates |
| 7 | Virus Control- Plastic (10 minute exposure) | 2 replicates |
| 8 | Virus Control- Cloth (10 minute exposure) | 2 replicates |
| 9 | Virus Control- Mesh (10 minute exposure) | 2 replicates |
| 10 | Virus Control- Plastic (60 minute exposure) | 2 replicates |
| 11 | Virus Control Cloth (60 minute exposure) | 2 replicates |
| 12 | Virus Control Mesh (60 minute exposure) | 2 replicates |

The Test Articles, Test Substrates and virus (SARS-CoV-2) were prepared according to protocol and each preparation was noted in the study notebook for this study.

Two experimental days were run for this study with the second day as run as a confirmatory. For Day 1, after coating the Test Substrates with PCA as described above (Groups shown in Table 1 above), a $TCID_{50}$ was performed at 10 minutes or 60 minutes after initial application of the virus. There was an observed log difference between the experimental groups (Group 1: Plastic-10 min, Group 2: Cloth-10 min, Group 3: Mesh-10 min, Group7: Plastic-60 min, Group 8: Cloth-60 min, Group 9: Mesh-60 min) when compared to the controls (Group 4: Plastic-10 min, Group 5: Cloth-10 min, Group 6: Mesh-10 min, Group 10:Plastic-60 min, Group 11: Cloth-60 min, Group 12: Mesh-60 min)

Day 1 results observed did indicate some log reductions in infectious virus titers under the experimental conditions performed for this study when compared to controls. The results are shown below in Table 2.

TABLE 2

| | | | | Initial Experimental Run Results. | | | |
|---|---|---|---|---|---|---|---|
| Group | Test Article/substrate | Replicate | Incubation time | $TCID_{50}$ $Log_{10}$/mL* | Log average | St.Dev. | log difference^ |
| 1 | PCA/plastic | 1 | 10 Min | 3.75 | 3.75 | 0.00 | −0.63 |
| | PCA/plastic | 2 | 10 min | 3.75 | | | |
| 2 | PCA/Cloth | 1 | 10 min | 2.75 | 2.75 | 0.00 | −1.25 |
| | PCA/Cloth | 2 | 10 min | 2.75 | | | |
| 3 | PCA/Mesh | 1 | 10 min | 3.50 | 3.38 | 0.18 | −0.25 |
| | PCA/Mesh | 2 | 10 min | 3.25 | | | |

TABLE 2-continued

Initial Experimental Run Results.

| Group | Test Article/substrate | Replicate | Incubation time | TCID$_{50}$ Log$_{10}$/mL* | Log average | St.Dev. | log difference^ |
|---|---|---|---|---|---|---|---|
| 4 | Control/plastic | 1 | 10 Min | 3.75 | 4.38 | 0.88 | N/A |
|   | Control/plastic | 2 | 10 min | 5.00 |  |  |  |
| 5 | Control/Cloth | 1 | 10 min | 3.75 | 4.00 | 0.35 | N/A |
|   | Control/Cloth | 2 | 10 min | 4.25 |  |  |  |
| 6 | Control/Mesh | 1 | 10 min | 3.75 | 3.63 | 0.18 | N/A |
|   | Control/Mesh | 2 | 10 min | 3.50 |  |  |  |
| 7 | PCA/plastic | 1 | 60 Min | 3.25 | 2.88 | 0.53 | −1.13 |
|   | PCA/plastic | 2 | 60 Min | 2.50 |  |  |  |
| 8 | PCA/Cloth | 1 | 60 Min | 2.50 | 2.75 | 0.35 | −1.00 |
|   | PCA/Cloth | 2 | 60 Min | 3.00 |  |  |  |
| 9 | PCA/Mesh | 1 | 60 Min | 1.00 | 1.50 | 0.71 | −2.00 |
|   | PCA/Mesh | 2 | 60 Min | 2.00 |  |  |  |
| 10 | Control/plastic | 1 | 60 Min | 3.75 | 4.00 | 0.35 | N/A |
|   | Control/plastic | 2 | 60 Min | 4.25 |  |  |  |
| 11 | Control/Cloth | 1 | 60 Min | 4.00 | 3.75 | 0.35 | N/A |
|   | Control/Cloth | 2 | 60 Min | 3.50 |  |  |  |
| 12 | Control/Mesh | 1 | 60 Min | 3.25 | 3.50 | 0.35 | N/A |
|   | Control/Mesh | 2 | 60 Min | 3.75 |  |  |  |
| 13 | Virus control (no coupon) | N/A | 10 min | 5.75 | N/A | N/A | N/A |
| 14 | Virus control (no coupon) | N/A | 60 min | 5.75 | N/A | N/A | N/A |

*limit of detection is 1.5 TCID$_{50}$ Log$_{10}$/mL
^Log difference is defined as the averaged TCID$_{50}$ Log$_{10}$/mL from virus control on substrates - TCID$_{50}$ Log$_{10}$/mL from replicate test group. Log difference indicates amount of reduction in infectious virus when comparing the virus control on substrate to the test group.

For Day 2, after coating the Test Substrates with PCA as described above (Groups shown in Table 1 above), a TCID$_{50}$ was performed at 10 minutes or 60 minutes after initial application of the virus. There was a modification to the procedures to see if the viral titers could be increased. To mitigate against evaporation during the incubation periods, these modifications included adding an additional 50 µl of DMEM on each side of the test substrate and a glass coverslip was placed on top of the test substrate. As with the Day 1 run, there was an observed log difference between the experimental groups (Group1: Plastic-10 min, Group 2: Cloth-10 min, Group 3: Mesh-10 min, Group7:Plastic-60 min, Group 8: Cloth-60 min, Group 9: Mesh-60 min) when compared to the controls (Group 4:Plastic-10 min, Group 5: Cloth-10 min, Group 6: Mesh-10 min, Group 10:Plastic-60 min, Group 11: Cloth-60 min, Group 12: Mesh-60 min) as shown in Table 3, thereby confirming the results from the Day 1 run.

TABLE 3

Confirmatory Experimental Run Results.

| Group | Test Article/substrate | Replicate | Incubation time | TCID$_{50}$ Log$_{10}$/mL* | Log average | St.Dev. | log difference^ |
|---|---|---|---|---|---|---|---|
| 1 | PCA/plastic | 1 | 10 Min | 4.25 | 4.38 | 0.18 | −1.13 |
|   | PCA/plastic | 2 | 10 min | 4.50 |  |  |  |
| 2 | PCA/Cloth | 1 | 10 min | 4.25 | 4.25 | 0.00 | −1.13 |
|   | PCA/Cloth | 2 | 10 min | 4.25 |  |  |  |
| 3 | PCA/Mesh | 1 | 10 min | 4.75 | 4.63 | 0.18 | −1.13 |
|   | PCA/Mesh | 2 | 10 min | 4.50 |  |  |  |
| 4 | Control/plastic | 1 | 10 Min | 5.50 | 5.50 | 0.00 | N/A |
|   | Control/plastic | 2 | 10 min | 5.50 |  |  |  |
| 5 | Control/Cloth | 1 | 10 min | 5.50 | 5.38 | 0.18 | N/A |
|   | Control/Cloth | 2 | 10 min | 5.25 |  |  |  |
| 6 | Control/Mesh | 1 | 10 min | 5.75 | 5.75 | 0.00 | N/A |
|   | Control/Mesh | 2 | 10 min | 5.75 |  |  |  |
| 7 | PCA/plastic | 1 | 60 Min | 3.50 | 3.63 | 0.18 | −1.50 |
|   | PCA/plastic | 2 | 60 Min | 3.75 |  |  |  |
| 8 | PCA/Cloth | 1 | 60 Min | 2.00 | 2.75 | 1.06 | −2.38 |
|   | PCA/Cloth | 2 | 60 Min | 3.50 |  |  |  |
| 9 | PCA/Mesh | 1 | 60 Min | 4.50 | 4.38 | 0.18 | −0.88 |
|   | PCA/Mesh | 2 | 60 Min | 4.25 |  |  |  |
| 10 | Control/plastic | 1 | 60 Min | 5.00 | 5.13 | 0.18 | N/A |
|   | Control/plastic | 2 | 60 Min | 5.25 |  |  |  |
| 11 | Control/Cloth | 1 | 60 Min | 4.50 | 5.13 | 0.88 | N/A |
|   | Control/Cloth | 2 | 60 Min | 5.75 |  |  |  |
| 12 | Control/Mesh | 1 | 60 Min | 5.25 | 5.25 | 0.00 | N/A |
|   | Control/Mesh | 2 | 60 Min | 5.25 |  |  |  |

TABLE 3-continued

Confirmatory Experimental Run Results.

| Test Group | Article/substrate | Replicate | Incubation time | TCID$_{50}$ Log$_{10}$/mL* | Log average | St.Dev. | log difference^ |
|---|---|---|---|---|---|---|---|
| 13 | Virus control (no coupon) | N/A | 10 min | 5.75 | N/A | N/A | N/A |
| 14 | Virus control (no coupon) | N/A | 60 min | 5.75 | N/A | N/A | N/A |

*limit of detection is 1.5 TCID$_{50}$ Log$_{10}$/mL
^Log difference is defined as the averaged TCID$_{50}$ Log$_{10}$/mL from virus control on substrates - TCID$_{50}$ Log$_{10}$/mL from replicate test group. Log difference indicates amount of reduction in infectious virus when comparing the virus control on substrate to the test group.

TABLE 4

Comparison between Initial Experimental Run to Confirmatory Run

| Test Article/substrate | Incubation time | Day 1: Log difference | Confirmatory: Log difference |
|---|---|---|---|
| PCA/plastic | 10 Min | −0.63 | −1.13 |
| PCA/Cloth | 10 min | −1.25 | −1.13 |
| PCA/Mesh | 10 min | −0.25 | −1.13 |
| PCA/plastic | 60 Min | −1.13 | −1.50 |
| PCA/Cloth | 60 min | −1.00 | −2.38 |
| PCA/Mesh | 60 min | −2.00 | −0.88 |

A PCA coating on the three test substrates, appeared to show some effectiveness in reducing infectious virus titers in the experimental condition shown in the protocol after the 10 minutes and 60 minutes post-exposure incubation when compared to the virus control on substrate. From both the Day 1 and the confirmatory runs, the log reduction varied between a 0.63 to a 2.38 log reduction.

Overall, these results show that PCA when coated approximately 24 hours prior to virus exposure can reduce infectious virus performance on a substrate, however, overall effectiveness was somewhat varied between runs and test substrate. Additionally, it appears that a longer incubation time may be marginally more effective than the shorter 10 minute time. A 1 to 2 log reduction/difference corresponds to a 90 to 99% inactivation while a 3 log reduction corresponds to a 99.9% inactivation.

Example 4

The second laboratory test utilized test coupons made of solid stainless steel, plastic and K95 mask were coated in 30% w/v PCA in 70% ethanol. Each coupon was dipped in PCA, allowed to dry, dipped again and allowed to dry with the opposite side of the coupon facing up. Once dry, 200 ul virus was added to each coupon and allowed to dry (45 minutes-1 h drying time). Virus was recovered by adding 2 ml DMEM/F12 media and washing the coupon, without scraping so as not to dislodge PCA crystals. A yellow color change in the media was observed indicating acidification of the media upon addition to the PA-coated coupon. The recovered virus was added to empty 96 well plates and diluted 1:10 down the plate. This was then added to Vero E6 cells that had grown to ~70% confluence. Cytotoxicity controls without virus and recovery controls without PCA were also done in the same manner. After addition to the cells, plates were read at day 4 for the presence of cytopathic effect (CPE) due to viral infection of cells. Note that cytotoxicity and CPE cannot be differentiated in this assay, thus any dead cells are marked as positive.

Cytotoxicity was seen up to 1:100 dilution for the K95, and 1:10 for the stainless steel and plastic coupons. Positive CPE for virus recovery controls was seen at least down to 1:10,000 dilutions for all 3 coupon materials, thus each coupon material was adequate for coupon testing. Results are shown in the table below. The SS=stainless steel, K95=K95 mask and P=plastic. +PCA means coupons coated with PCA. No PCA (e.g. SS-1) indicates virus recovery controls with no PCA coating that had virus dried and recovered.

TABLE 5

| Sample Name | Replicate # | TCID50 | TCID50/mL | Log10 TCID50 | Average TCID50 | Average Log10 TCID50 | Log Reduction to Virus Controls | Percent Log Reduction |
|---|---|---|---|---|---|---|---|---|
| SS+PCA-1 | 1 | 501.1872 | 0.01995262 | 2.70 | 298.9493 | 2.37 | 2.93 | 99.88% |
| SS+PCA-2 | 2 | 79.43282 | 0.12589254 | 1.90 | | | | |
| SS+PCA-3 | 3 | 316.2278 | 0.03162278 | 2.50 | | | | |
| SS-1 | 1 | 87992.25 | 0.00011365 | 4.94 | 226075.8 | 5.29 | | |
| SS-2 | 2 | 316227.8 | 3.1623E−05 | 5.50 | | | | |
| SS-3 | 3 | 274007.4 | 3.6495E−05 | 5.44 | | | | |
| K95+PCA-1 | 1 | 316.2278 | 0.03162278 | 2.50 | 182.4589 | 2.10 | 2.45 | 99.65% |
| K95+PCA-2 | 2 | 199.5262 | 0.05011872 | 2.30 | | | | |
| K95+PCA-3 | 3 | 31.62278 | 0.31622777 | 1.50 | | | | |
| K95-1 | 1 | 58230.63 | 0.00017173 | 4.77 | 39285.11 | 4.55 | | |
| K95-2 | 2 | 19952.62 | 0.00050119 | 4.30 | | | | |
| K95-3 | 3 | 39672.07 | 0.00025207 | 4.60 | | | | |
| P+PCA-1 | 1 | 50.11872 | 0.19952623 | 1.70 | 88.00117 | 1.91 | 3.94 | 99.99% |
| P+PCA-2 | 2 | 125.8925 | 0.07943282 | 2.10 | | | | |
| P+PCA-3 | 3 | 87.99225 | 0.11364637 | 1.94 | | | | |

TABLE 5-continued

| Sample Name | Replicate # | TCID50 | TCID50/mL | Log10 TCID50 | Average TCID50 | Average Log10 TCID50 | Log Reduction to Virus Controls | Percent Log Reduction |
|---|---|---|---|---|---|---|---|---|
| P-1 | 1 | 1217075 | 8.2164E−06 | 6.09 | 971841.2 | 5.86 | | |
| P-2 | 2 | 203950 | 4.9032E−05 | 5.31 | | | | |
| P-3 | 3 | 1494498 | 6.6912E−06 | 6.17 | | | | |

Table 6. The following are the results when the SARS CoV 2 virus was delivered in aqueous droplet on the PCA coated article immediately after drying. The virucidal effect was measured at 2 hours in this test.

| Sample Name | Replicate # | TCID50 | Log10 TCID50 | Average TCID50 | Average Log10 TCID50 | Log Reduction to Virus Controls | Percent Log Reduction |
|---|---|---|---|---|---|---|---|
| SS+PCA-1 | 1 | 5.01E+01 | 1.7 | 60.0702 | 1.77 | 2.33 | 99.53% |
| SS+PCA-2 | 2 | 5.84E+01 | 1.77 | | | | |
| SS+PCA-3 | 3 | 7.17E+01 | 1.86 | | | | |
| SS-1 | 1 | 7.94E+03 | 3.9 | 13495.05 | 4.1 | | |
| SS-2 | 2 | 1.26E+04 | 4.1 | | | | |
| SS-3 | 3 | 2.00E+04 | 4.3 | | | | |
| K95+PCA-1 | 1 | 3.16E+01 | 1.5 | | | | |
| K95+PCA-2 | 2 | 3.16E+01 | 1.5 | 31.62278 | 1.5 | 2.35 | 99.55% |
| K95+PCA-3 | 3 | 3.16E+01 | 1.5 | | | | |
| K95-1 | 1 | 5.01E+03 | 3.7 | | | | |
| K95-2 | 2 | 7.94E+03 | 3.9 | 7251.46 | 3.85 | | |
| K95-3 | 3 | 8.80E+03 | 3.94 | | | | |
| P+PCA-1 | 1 | 5.84E+01 | 1.77 | | | | |
| P+PCA-2 | 2 | 5.01E+01 | 1.7 | 46.72521 | 1.66 | 2.71 | 99.81% |
| P+PCA-3 | 3 | 3.16E+01 | 1.5 | | | | |
| P-1 | 1 | 1.26E+04 | 4.1 | | | | |
| P-2 | 2 | 3.16E+04 | 4.5 | 25278.27 | 4.37 | | |
| P-3 | 3 | 3.16E+04 | 4.5 | | | | |

This study shows the continued effectiveness of the PCA coating up to and including 2 hours with a 99%+Log reduction.

While this disclosure includes specific examples, it will be apparent after an understanding of the disclosure of this application has been attained that various changes in form and details may be made in these examples without departing from the spirit and scope of the claims and their equivalents.

I claim:

1. A method of treating Covid-19 in a mammal comprising: administering to the mammal in need thereof a composition comprising protocatechuic acid.

2. The method of claim 1, wherein the mammal is a human.

3. The method of claim 1, wherein the protocatechuic acid comprises protocatechuic acid crystals.

4. The method of claim 1, wherein the composition comprises a pharmaceutically acceptable carrier.

5. The method of claim 4, wherein the pharmaceutically acceptable carrier is a biodegradable microsphere or a slow release bioabsorbable material.

6. The method of claim 4, wherein the pharmaceutically acceptable carrier comprises D,L lactide/glycolide.

7. The method of claim 4, wherein the administering is via topical, oral, buccal, injection, intravenous, peritoneal, inhalant, subcutaneous, sublingual, and/or transdermal administration.

8. The method of claim 1, wherein the administering to the mammal is oral administration.

9. The method of claim 8, wherein the oral administration dosage of protocatechuic acid is a minimum of 500 to about 1000 milligrams per day.

10. The method of claim 1, wherein the administering to the mammal is through intravenous administration.

11. The method of claim 10, wherein the administration includes 50 mg/kg of protocatechuic acid every 6 hours for 4 days.

12. The method of claim 1, wherein the administering to the mammal is through intraperitoneal administration.

13. The method of claim 1, wherein the administration to the mammal comprises coating of skin, oral cavity, nares, nasopharynx, and/or pulmonary tree with the composition comprising protocatechuic acid.

14. The method of claim 1, wherein the administering to mammal is through a liquid spray, aerosol spray, and/or fog.

15. The method of claim 14, wherein the composition further comprises a liquid vehicle and a stabilizer.

16. The method of claim 15, wherein the liquid vehicle is water.

17. The method of claim 15, wherein the stabilizer is an essential oil.

18. The method of claim 14, wherein the administration is to the skin.

19. The method of claim 14, wherein the administration is to the lungs.

20. The method of claim 14, wherein the administration is to the nasal cavity.

* * * * *